US009036781B1

(12) United States Patent
Safai (10) Patent No.: US 9,036,781 B1
(45) Date of Patent: May 19, 2015

(54) AMPLIFIED BACKSCATTER X-RAY INSPECTION SYSTEM (71) Applicant: The Boeing Company, Chicago, IL (US)

(72) Inventor: Morteza Safai, Newcastle, WA (US)

(73) Assignee: THE BOEING COMPANY, Chicago, IL (US)

( * ) Notice: Subject to any disclaimer, the term of this patent is extended or adjusted under 35 U.S.C. 154(b) by 251 days.

(21) Appl. No.: 13/650,733

(22) Filed: Oct. 12, 2012

(51) Int. Cl.
*G01N 23/201* (2006.01)
*G01N 23/00* (2006.01)

(52) U.S. Cl.
CPC ...................... *G01N 23/00* (2013.01)

(58) Field of Classification Search
USPC ............................................. 378/86
See application file for complete search history.

(56) References Cited

U.S. PATENT DOCUMENTS

| 3,621,527 | A  | * | 11/1971 | Johnston et al. ................. 425/79 |
| 8,325,871 | B2 | * | 12/2012 | Grodzins et al. .............. 376/153 |
| 2006/0261290 | A1 | * | 11/2006 | Wilhelmus Van Herpen et al. .......................... 250/492.2 |
| 2007/0025512 | A1 | * | 2/2007 | Gertsenshteyn et al. ....... 378/86 |
| 2009/0136739 | A1 | * | 5/2009 | Ruuttu et al. ................. 428/323 |

OTHER PUBLICATIONS

Bougeant, "Alternative Techniques of Backscatter Radiography: Snapshot Aperture Backscatter Radiography and Collimated Segmented Detector Scatter X-Ray Imaging," Thesis, University of Florida, Aug. 2009, 111 pages.

* cited by examiner

*Primary Examiner* — Phillip A Johnston
(74) *Attorney, Agent, or Firm* — Yee & Associates, P.C.

(57) ABSTRACT

A method and apparatus for inspecting an object. A radiation generation system is configured to emit radiation. A detector system is configured to detect backscatter formed in response to the radiation encountering the object. A redirection system is positioned relative to the detector system and is configured to redirect the backscatter to the detector system.

20 Claims, 10 Drawing Sheets

Amplified Backscatter X-Ray Inspection System

AMPLIFIED BACKSCATTER X-RAY INSPECTION SYSTEM

BACKGROUND INFORMATION

1. Field

The present disclosure relates generally to inspection systems and, in particular, to backscatter x-ray inspection systems. Still more particularly, the present disclosure relates to a method and apparatus for increasing the amount of backscatter detected off of an object.

2. Background

A backscatter x-ray inspection system is an example of a nondestructive inspection system that uses x-rays to inspect an object. Some currently available backscatter x-ray inspection systems include an x-ray tube, a collimator, and a detector. The x-ray tube generates and emits x-rays. The collimator filters these x-rays to form an x-ray beam using a portion of the x-rays that travel substantially parallel to a specified direction.

When the x-ray beam encounters the object, some or all of the x-rays in the x-ray beam are not absorbed by the object. Some or all of the x-rays may be scattered by the object. In particular, the x-rays may be scattered off of the surface of the object, the portion of the object under the surface of the object, or a combination of the two. The scattered x-rays are referred to as backscatter.

The detector detects some or all of this backscatter. The detected backscatter may be used to generate image data for the object. This image data may be used to form one or more images of the object. For example, the backscatter detected when the x-ray beam is directed at a particular location on the object may be used to generate an intensity value for a pixel in an image that corresponds to that particular location on the object.

The x-ray beam may be moved along the object in a selected pattern such as, for example, a raster pattern, such that the image data may be generated for different locations on the object. In one illustrative example, the direction in which the x-ray beam is pointed may be changed such that the angle of incidence of the x-ray beam, with respect to the object, changes. This image data is used to form one or more images of the object that may be used to determine whether any inconsistencies are present in the object.

Many currently used detectors for backscatter x-ray inspection systems include photomultiplier tubes with plastic scintillators. These types of detectors are typically located behind the x-ray tube. These detectors are configured to detect x-ray photons that are returned from a scattering effect of the x-ray beam directed toward the object being inspected.

The x-ray sources used for backscatter x-ray inspection systems may have various ranges of energy levels used to generate x-ray beams. For example, some sources of x-rays may have energy levels of up to around 400 keV. With these types of systems, x-ray photons in the backscatter may have an energy level from about 70 keV to about 450 keV. This range may be a spectrum of x-ray photons that may be present in the backscatter. The energy of the x-ray photons may depend on factors such as, for example, the scattering angle, Bremsstrahlung x-ray distribution, and other suitable factors.

The Bremsstrahlung x-ray distribution for x-ray photons has a spectrum that may vary from low energy at the low end of the spectrum to high energy at the high end of the spectrum. For example, an 80 keV beam may result in backscatter distributed in a spectrum from about 15 keV to about 80 keV.

This distribution of x-ray photons increases the difficulty in designing a detector for detecting backscatter x-ray photons as efficiently as desired. For example, the detector may more easily absorb x-ray photons in the middle of the spectrum. Lower energy photons in the spectrum may not penetrate the surface of the detector. Higher energy photons in the spectrum may travel all the way through the detector and may never be absorbed by the scintillator.

Currently, one manner in which this inefficiency is overcome is through increasing the size of the power supply for the x-ray source. The power supply may be increased such that sufficient x-ray photon flux to produce energy for x-ray photons in a desired range of the Bremsstrahlung x-ray distribution that can be detected by the detector may be produced. This larger power supply usually results in a larger x-ray tube. The increase in the size of the power supply and the x-ray tube increases the expense, size, and weight of the backscatter x-ray inspection system.

Therefore, it would be desirable to have a method and apparatus that takes into account at least some of the issues discussed above, as well as other possible issues.

SUMMARY

In one illustrative embodiment, an apparatus comprises a radiation generation system, a detector system, and redirection system. The radiation generation system is configured to emit radiation. The detector system is configured to detect backscatter formed in response to the radiation encountering an object. The redirection system is positioned relative to the detector system and is configured to redirect the backscatter to the detector system.

In another illustrative embodiment, a method for inspecting an object is present. Radiation is emitted from a radiation source. Backscatter is redirected from the radiation encountering the object to a detector system using a redirection system positioned relative to the detector system.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that a good detector for detecting x-ray photons in backscatter is a detector that detects x-ray photons in a larger range of energy levels than currently possible. For example, it would be desirable to have a detector that may detect x-ray photons that are scattered from the low end through the high end in a spectrum of levels of x-ray energy in a Bremsstrahlung x-ray distribution.

The illustrative embodiments recognize and take into account that many detection systems are used to count the number of x-ray photons in the backscatter from a particular location. With these types of systems, counting an x-ray photon more than once is undesirable.

The illustrative embodiments also recognize and take into account that with respect to generating images, the concern with counting x-ray photons may be absent. As a result, the illustrative embodiments recognize and take into account that counting x-ray photons more than once may be desirable when generating images of an object.

Thus, the illustrative embodiments provide a method and apparatus for an amplified x-ray backscatter inspection system. In one illustrative embodiment, an apparatus comprises a radiation system, a detector system, and a redirection system. The radiation system is configured to emit radiation. The detector system is configured to detect backscatter formed in response to the radiation encountering an object. The redirection system is positioned relative to the detector system. The redirection system is configured to redirect the backscatter to the detector system. The redirection system may function as an amplifier that causes the detector system to detect more backscatter than possible without the redirection system.

With the redirection of backscatter, an x-ray photon in the backscatter may generate light more than once. In other words, more than one light photon or signal may be generated by an x-ray photon. The illustrative embodiments recognize and take into account that with generating image data from backscatter, counting light generated by an x-ray photon more than once is not detrimental to generating the image.

Figure 1:
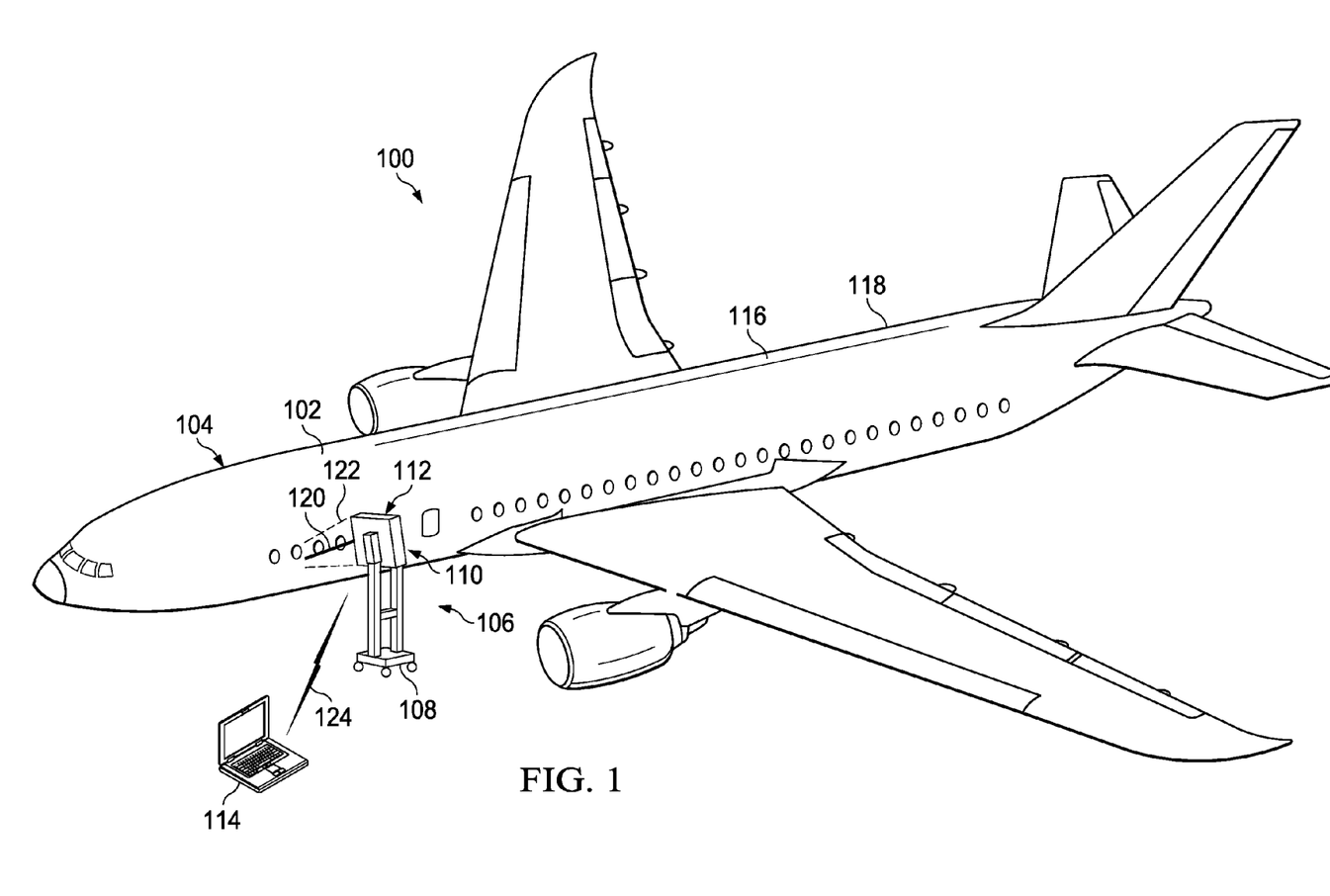
FIG. 1 is an illustration of an inspection environment in accordance with an illustrative embodiment.

With reference now to the figures and, in particular, with reference to FIG. 1, an illustration of an inspection environment is depicted in accordance with an illustrative embodiment. In this depicted example, inspection environment 100 is an example of an environment in which object 102 in the form of aircraft 104 may be inspected.

In this illustrative example, the inspection of aircraft 104 may be performed using backscatter inspection system 106. As depicted, backscatter inspection system 106 includes moveable platform 108, radiation generation system 110, detector system 112, and computer 114.

As depicted, radiation generation system 110 and detector system 112 are associated with moveable platform 108. When one component is "associated" with another component, the association is a physical association in these depicted examples. For example, a first component, radiation generation system 110, may be considered to be associated with a second component, moveable platform 108, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

Radiation generation system 110 is configured to generate x-rays and direct a portion of the x-rays toward surface 116 of fuselage 118 of aircraft 104. In particular, radiation generation system 110 may direct x-ray beam 120 toward surface 116 of fuselage 118 of aircraft 104.

As depicted, surface 116 is an exterior surface of fuselage 118. X-ray beam 120 may at least partially penetrate surface 116 of fuselage 118 of aircraft 104. Detector system 112 is configured to detect backscatter 122 that may be generated in response to x-ray beam 120 encountering surface 116 of fuselage 118. In these illustrative examples, backscatter 122 comprises x-ray photons that may be generated in response to x-ray beam 120 encountering fuselage 108. In particular, backscatter 122 may be formed in response to at least a portion of x-ray beam 120 encountering at least one of surface 116 and the interior of fuselage 108 in these illustrative examples. In other words, backscatter 122 from surface 116, the interior of fuselage 108, or both surface 116 and the interior of fuselage 108 may be detected by detector system 112.

As depicted, detector system 112 may be configured in accordance with an illustrative embodiment in a manner that may increase the amount of backscatter 122 detected by detector system 112. Detector system 112 may generate image data in response to detecting backscatter 122. This image data may be sent to computer 114 over wireless communications link 124. By increasing the amount of backscatter 122 detected by detector system 112, the image data generated by detector system 112 may generate images for computer 114 with a desired level of quality.

Figure 2:
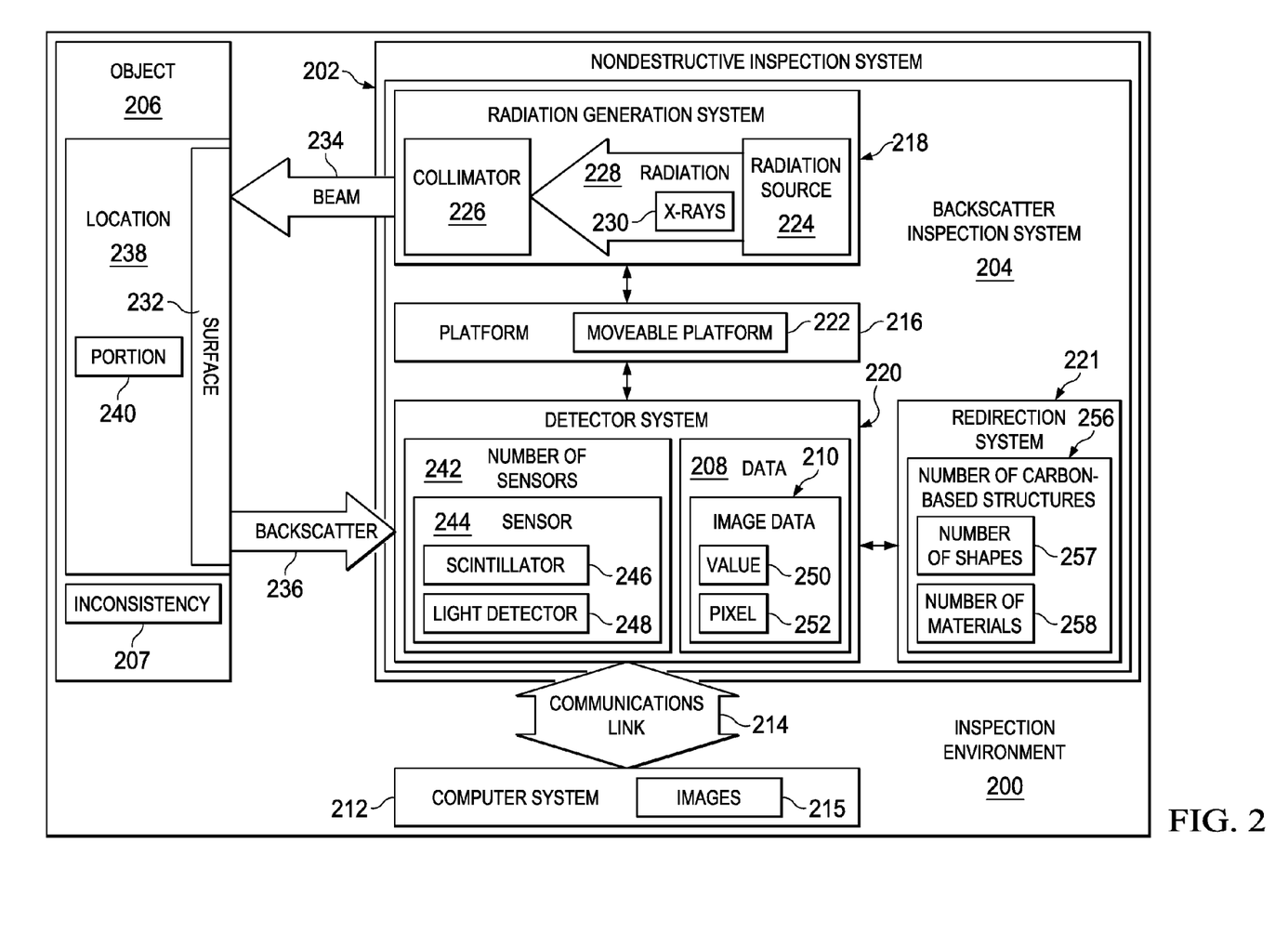
FIG. 2 is an illustration of a block diagram of an inspection environment in accordance with an illustrative embodiment.

With reference now to FIG. 2, an illustration of a block diagram of an inspection environment is depicted in accordance with an illustrative embodiment. In this depicted example, inspection environment 100 in FIG. 1 is an example of one physical implementation for inspection environment 200 shown in block form in FIG. 2.

In this illustrative example, inspection environment 200 includes nondestructive inspection system 202. In particular, nondestructive inspection system 202 takes the form of backscatter inspection system 204.

In these illustrative examples, backscatter inspection system 204 may be used to perform inspection of object 206. Object 206 may take various forms in addition to aircraft 104 shown in FIG. 1. For example, object 206 may be selected from one of a mobile platform, a stationary platform, a land-based structure, an aquatic-based structure, a space-based structure, a surface ship, a tank, a personnel carrier, a train, a spacecraft, a space station, a satellite, a submarine, an automobile, a power plant, a bridge, a dam, a house, a manufacturing facility, a building, a fuselage, a composite part, a composite fuselage section, an engine housing, a wing, a horizontal stabilizer, a vertical stabilizer, a wall, a gas pipeline, a container, a person, a circuit board, a piece of luggage, and other suitable types of objects.

In these illustrative examples, backscatter inspection system 204 is configured to inspect object 206 without causing an undesired effect to object 206. For example, backscatter inspection system 204 may perform inspection of object 206 without causing physical alterations to object 206.

In these illustrative examples, this inspection may be performed to determine whether inconsistency 207 is present in object 206. Inconsistency 207 may be any deviation within object 206 from a desired state of object 206. For example, inconsistency 207 may be a crack, a void, delamination, or other undesired features.

As depicted, backscatter inspection system 204 is configured to generate data 208 about object 206 during inspection of object 206. Data 208 may include, for example, image data 210 for object 206.

Data 208 may be sent to computer system 212. Computer system 212 may comprise one or more computers. When more than one computer is present, those computers may be in communication with each other over a communications medium such as a network.

In this illustrative example, image data 210 may be sent by backscatter inspection system 204 to computer system 212 over communications link 214. Communications link 214 may be a wired link, a wireless link, an optical link, or any other suitable type of communications link. Computer system 212 is configured to receive and process data 208 generated by backscatter inspection system 204. In these illustrative examples, computer system 212 may generate images 215 of object 206 using image data 210.

In this illustrative example, backscatter inspection system 204 includes platform 216, radiation generation system 218, detector system 220, and redirection system 221. One or both of radiation generation system 218 and detector system 220 may be mounted on platform 216.

Platform 216 may be moveable platform 222. Moveable platform 222 may include a movement system or may be moved by a human operator or other vehicle depending on the particular implementation.

As depicted, moveable platform 222 may provide movement for radiation generation system 218 and detector system 220. This movement may be translation, rotation, or a combination of the two.

Moveable platform 222 may include movement devices, such as, for example, without limitation, wheels, rollers, sliders, a track system, and other types of movement devices. These movement devices may allow moveable platform 222 to be moved on a surface such as a floor, a rail system, or any other suitable type of surface.

As depicted, radiation generation system 218 may comprise radiation source 224 and collimator 226. Radiation source 224 and collimator 226 may be located within a structure such as a collimation wheel or other device, depending on the particular implementation.

Radiation source 224 is configured to generate radiation 228. Radiation generation system 218 is configured to emit radiation 228. Radiation 228 in this illustrative example may take the form of x-rays 230. X-rays 230 may be directed toward surface 232 of object 206.

In these illustrative examples, collimator 226 may be associated with at least one of platform 216 and radiation source 224. As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C or item B and item C.

Collimator 226 is a device configured to filter x-rays 230 such that only a portion of x-rays 230 traveling parallel to a desired direction pass through collimator 226. In particular, collimator 226 may use a portion of radiation 228 to form beam 234 of radiation 228. In these illustrative examples, beam 234 of radiation 228 is beam 234 of x-rays 230.

In this illustrative example, detector system 220 is configured to detect backscatter 236 formed in response to radiation 228 encountering object 206. Backscatter 236 may be generated by beam 234 encountering object 206.

As depicted, beam 234 may encounter object 206 at location 238 on surface 232 of object 206. Backscatter 236 may be formed in response to at least a portion of x-rays 230 in beam 234 encountering at least one of surface 232 and portion 240 under surface 232 of object 206.

In these illustrative examples, detector system 220 is configured to detect backscatter 236. As depicted, detector system 220 may be comprised of number of sensors 242. As used herein, a "number of" when used with reference to items means one or more items. For example, number of sensors 242 is one or more sensors.

In these illustrative examples, number of sensors 242 may be implemented in a number of different ways. For example, sensor 244 in number of sensors 242 may be comprised of scintillator 246 and light detector 248.

Scintillator 246 includes a material configured to generate light when encountering x-ray photons in backscatter 236. Light detector 248 is configured to measure the light emitted from scintillator 246. In particular, light detector 248 may detect the number of photons emitted by scintillator 246. Light detector 248 may take a number of different forms. For example, light detector 248 may be selected from at least one of a photomultiplier tube, a photo-electric sensor, a photodiode, or some other suitable type of light detector.

In this manner, number of sensors 242 may generate value 250 for pixel 252 from the detection of backscatter 236. Pixel 252 in this illustrative example corresponds to location 238 on object 206. In this manner, the different values for pixels generated by number of sensors 242 in detector system 220 may form image data 210 in data 208.

In these illustrative examples, redirection system 221 is positioned relative to detector system 220. Redirection system 221 is configured to redirect backscatter 236 to detector system 220.

In particular, redirection system 221 may redirect a portion of backscatter 236 that may not be absorbed by detector system 220. For example, redirection system 221 may redirect a portion of backscatter 236 that is reflected off of detector system 220, passes through detector system 220, or is otherwise not absorbed by detector system 220 in a manner that allows detector system 220 to generate values for pixels in image data 210.

In these illustrative examples, redirection system 221 is comprised of number of carbon-based structures 256. As depicted, number of carbon-based structures 256 in redirection system 221 may be associated with detector system 220.

In these illustrative examples, number of carbon-based structures 256 may have number of shapes 257. Number of shapes 257 for number of carbon-based structures 256 may be selected from at least one of a panel, a flat panel, a curved panel, a portion of a hollow sphere, a portion of a hollow cube, a housing, a frame, or other suitable forms.

Number of carbon-based structures 256 is comprised of number of materials 258. Number of materials 258 may be selected as any material that may redirect backscatter 236. In these illustrative examples, number of materials 258 may be selected as a material having a carbon-based structure. This type of material is referred to as a carbon-based material.

Number of materials 258 may be selected from at least one of a carbon-based material, a polymer, a polyurethane, a plastic, a hydrocarbon-based material, and any other suitable type of carbon-based material that is configured to redirect backscatter 236. When more than one type of material is present in number of materials 258, number of materials 258 may be arranged in layers.

In these illustrative examples, number of materials 258 may be selected as one or more materials in which a chain of organic units are present. These organic units may be polymer chains. X-ray photons and backscatter 236 may be redirected by the polymer chains in number of materials 258 more desirably as compared to other types of materials.

In these illustrative examples, redirection system 221 may be configured to redirect backscatter 236 that has an energy level from about 70 keV to about 450 keV to detector system 220. Of course, redirection system 221 may be configured to redirect backscatter 236 having other ranges of energy levels depending on the particular implementation. In some illustrative examples, this redirection of backscatter 236 may be referred to as scattering of backscatter 236.

With redirection system 221, greater amounts of backscatter 236 may be detected by number of sensors 242 in detector system 220. As greater amounts of backscatter 236 are redirected to number of sensors 242, an increase in the contrast of images 215 may be achieved. The number photons in backscatter 236 that are detected by number of sensors 242 is proportional to the contrast in images 215. Additionally, by increasing the number of photons detected by number of sensors 242, requirements for more a powerful x-ray source, power supply, or both are reduced.

In these illustrative examples, redirection system 221 may be included in backscatter inspection system 204 when backscatter inspection system 204 is initially manufactured. In other illustrative examples, redirection system 221 may be added to backscatter inspection system 204 when backscatter inspection system 204 is an already existing inspection system.

The illustration of inspection environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative examples, radiation source 224 may generate radiation 228 in other forms other than x-rays 230. For example, radiation source 224 may generate radiation 228 in the form of gamma rays and other suitable types of radiation that may be used to inspect object 206.

In other illustrative examples, number of sensors 242 may be implemented using other types of devices in addition to or in place of scintillator 246 and light detector 248. For example, number of sensors 242 may include charge-coupled devices that generate value 250 for pixel 252 based on backscatter 236 detected by the charge-coupled device. In yet other illustrative examples, redirection system 221 may be considered a component within detector system 220.

Figure 3:
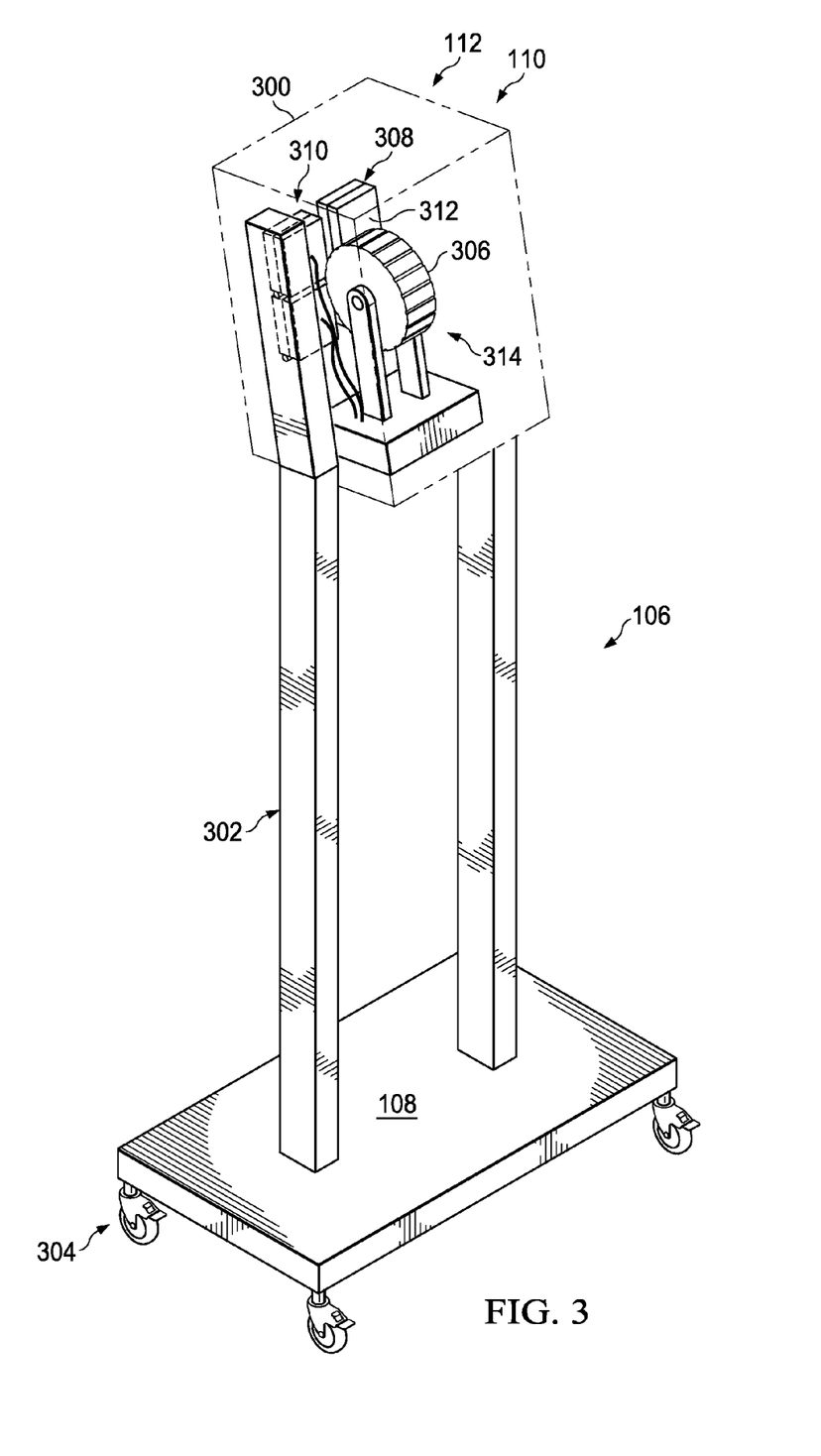
FIG. 3 is a more detailed illustration of a backscatter inspection system in accordance with an illustrative embodiment.

Turning now to FIG. 3, a more detailed illustration of a backscatter inspection system is depicted in accordance with an illustrative embodiment. As depicted, a more detailed view of backscatter inspection system 106 is shown in this figure. In this view, backside 314 of radiation generation system 110 and detector system 112 is shown.

Moveable platform 108 includes housing 300, stand 302, and wheels 304. As shown in this illustrative example, radiation generation system 110 and detector system 112 are associated with housing 300. In particular, these two components in backscatter inspection system 106 may be located in the interior of housing 300.

As depicted, housing 300 is shown in phantom such that radiation generation system 110 and detector system 112 can be seen within housing 300.

As depicted, radiation generation system 110 comprises collimation wheel 306 with a collimator and a radiation source within collimation wheel 306. In this illustrative example, the collimator is positioned in front of the radiation source within collimation wheel 306. Detector system 112 comprises number of sensors 308.

As depicted, redirection system 310 is comprised of carbon-based structures in the form of polymer structures 312. Polymer structures 312 are associated with number of sensors 308. In these illustrative examples, redirection system 310 with polymer structures 312 is configured to redirect backscatter 122 in FIG. 1 to number of sensors 308 in detector system 112. In these illustrative examples, redirection system 310 is configured to amplify backscatter 122 by increasing the amount of backscatter 122 that can be detected by detector system 112. In other words, this amplification of backscatter 122 may occur when redirection system 310 redirects some of backscatter 122 that has passed through detector system 112 back into detector system 112.

Figure 4:
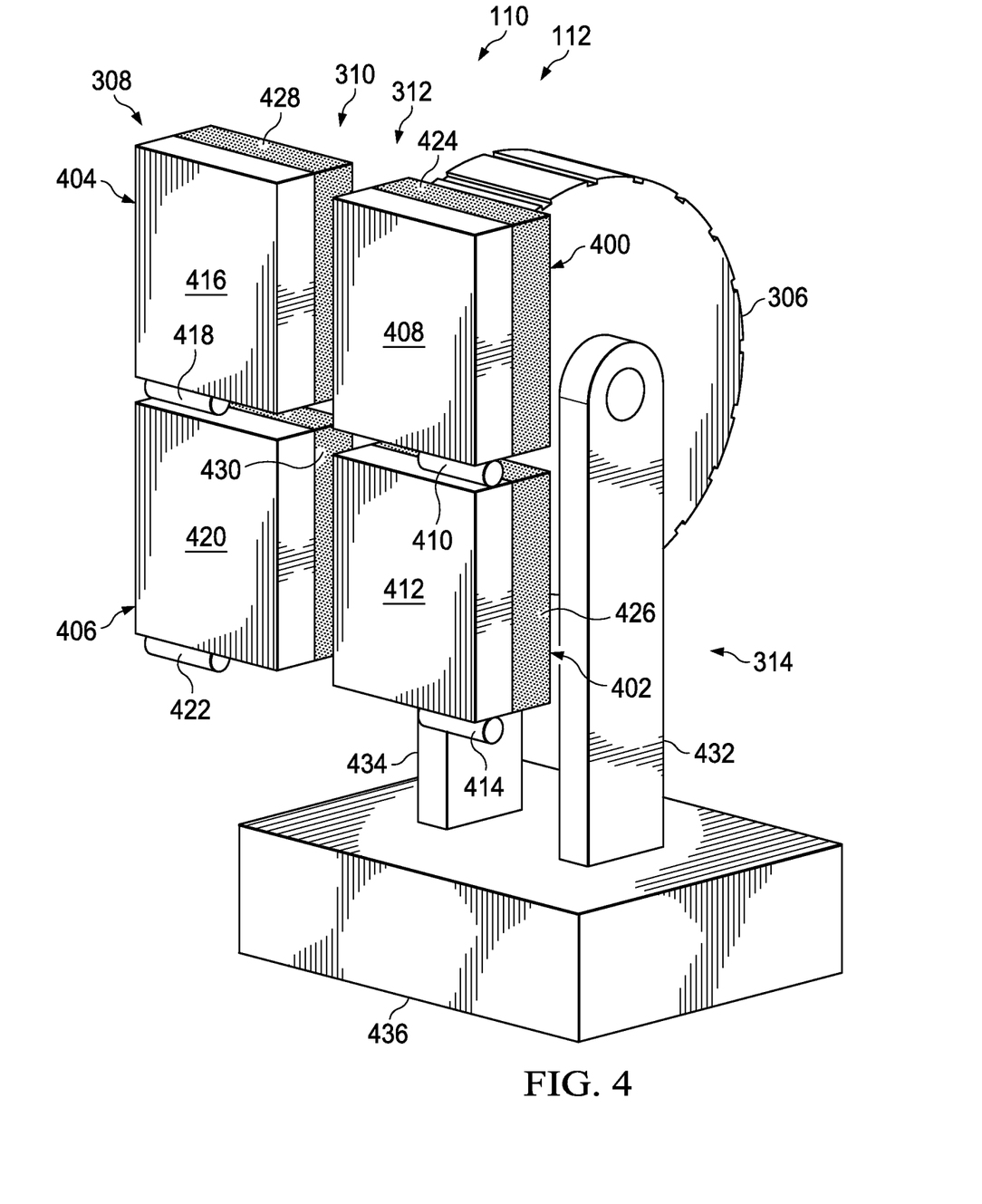
FIG. 4 is an illustration of a radiation generation system and a detector system in accordance with an illustrative embodiment.

With reference next to FIG. 4, an illustration of a radiation generation system and a detector system is depicted in accordance with an illustrative embodiment. In this depicted example, an isometric view of backside 314 of radiation generation system 110 and detector system 112 is shown without other components in backscatter inspection system 106 in FIG. 1.

In this isometric view, sensor 400, sensor 402, sensor 404, and sensor 406 in number of sensors 308 can be seen in detector system 112. As depicted, sensor 400 is comprised of scintillator 408 and photomultiplier 410. Sensor 402 is comprised of scintillator 412 and photomultiplier 414. Sensor 404 is comprised of scintillator 416 and photomultiplier 418. Sensor 406 is comprised of scintillator 420 and photomultiplier 422.

In these illustrative examples, scintillator 408, scintillator 412, scintillator 416, and scintillator 420 are configured to generate light in response to absorbing energy from backscatter 122 in FIG. 1.

As depicted, scintillator 408, scintillator 412, scintillator 416, and scintillator 420 may be comprised of different types of materials. The materials selected may be any material that has a luminescence property when struck by radiation such as x-ray photons. For example, a material may be selected from one of anthracene, stilbene, naphthalene, polyethylene naphthalate, and other suitable materials.

In these illustrative examples, photomultiplier 410, photomultiplier 414, photomultiplier 418, and photomultiplier 422 are configured to generate electrical signals in response to detecting light signals. These components in number of sensors 308 may be implemented using any currently available photomultiplier.

Also seen in this view are polymer structure 424, polymer structure 426, polymer structure 428, and polymer structure 430 in polymer structures 312 in redirection system 310. As depicted, polymer structure 424 is positioned relative to sensor 400. Polymer structure 426 is positioned relative to sensor 402. Polymer structure 428 is positioned relative to sensor 404. Polymer structure 430 is positioned relative to sensor 406. In these illustrative examples, polymer structures 312 are in contact with number of sensors 308. In other illustrative examples, a gap may be present between polymer structures 312 and number of sensors 308.

In these illustrative examples, polymer structure 424, polymer structure 426, polymer structure 428, and polymer structure 430 are connected to arm 432 and arm 434 on base 436. In turn, sensor 400, sensor 402, sensor 404, and sensor 406 are connected to polymer structure 424, polymer structure 426, polymer structure 428, and polymer structure 430, respectively.

In these illustrative examples, sensor 400 and sensor 402 also may be connected to arm 432 in addition to being connected to polymer structure 424 and polymer structure 426 or in place of being connected to polymer structure 424 and polymer structure 426. In a similar fashion, sensor 404 and sensor 406 also may be connected to arm 434 in addition to being connected to polymer structure 428 and polymer structure 430 or in place of being connected to polymer structure 428 and polymer structure 430.

Figure 5:
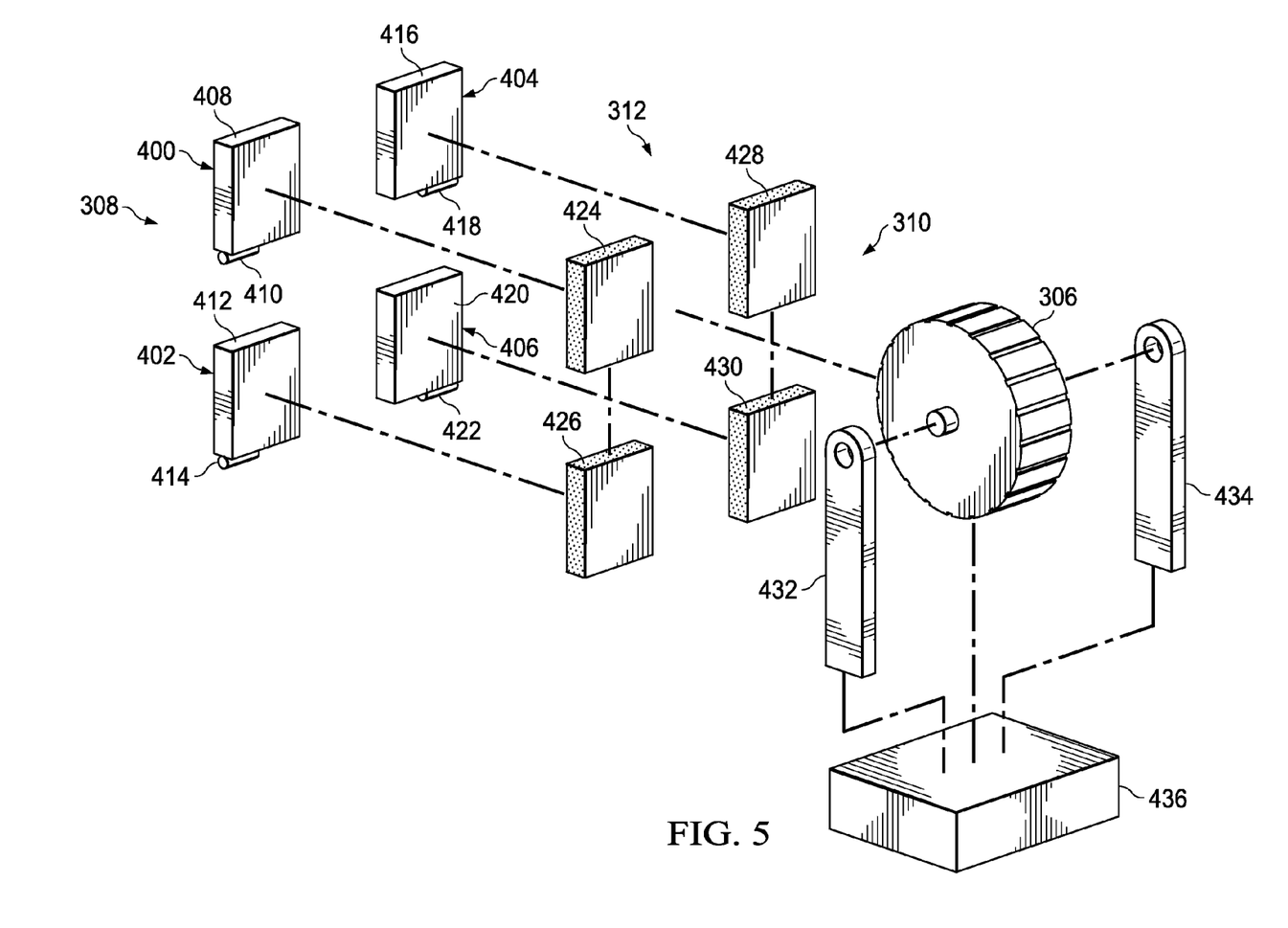
FIG. 5 is an illustration of an exploded view of a radiation generation system and a detector system in accordance with an illustrative embodiment.

Turning now to FIG. 5, an illustration of an exploded view of a radiation generation system and a detector system is depicted in accordance with an illustrative embodiment.

Figure 6:
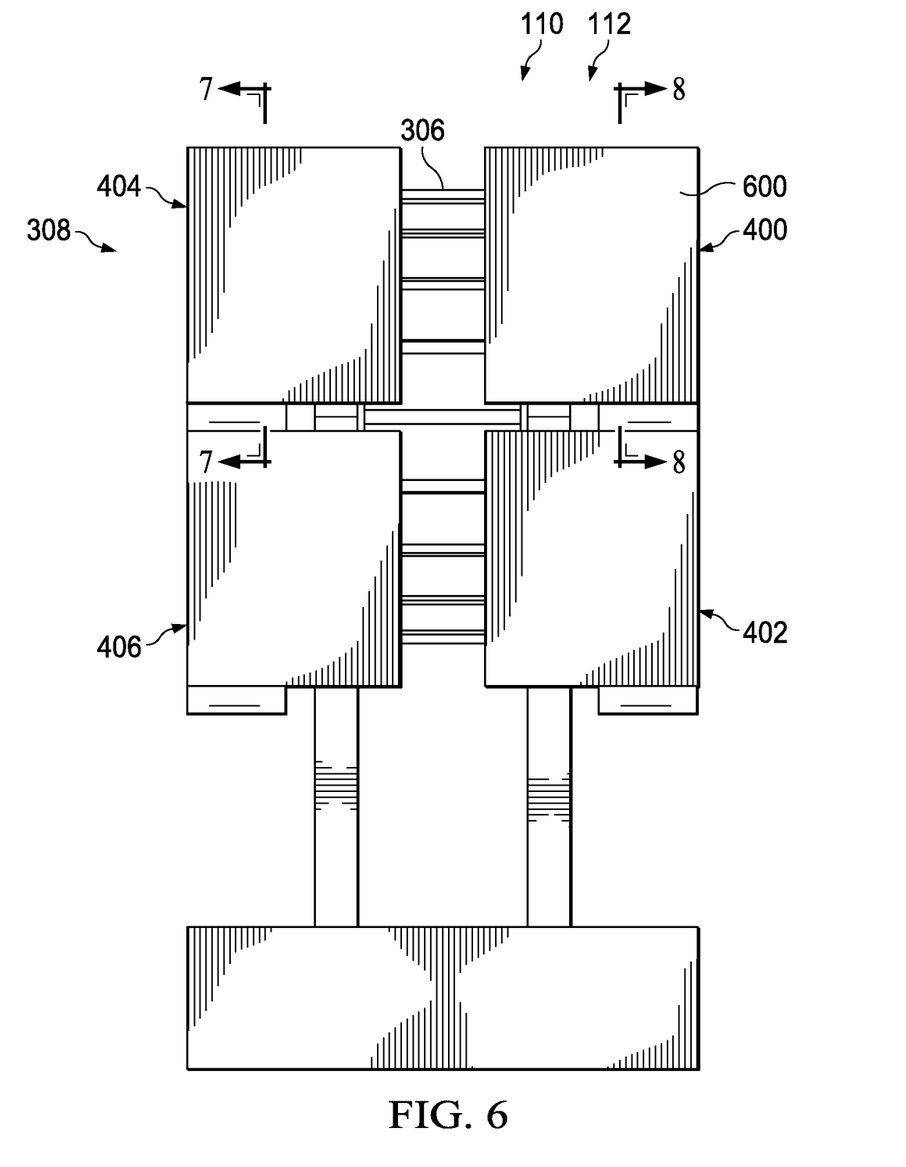
FIG. 6 is an illustration of a front view of a radiation generation system and a detector system in accordance with an illustrative embodiment.

Turning now to FIG. 6, an illustration of a front view of a radiation generation system and a detector system is depicted in accordance with an illustrative embodiment. In this depicted example, front side 600 of radiation generation system 110 and detector system 112 are seen in this view. Front side 600 of radiation generation system 110 and detector system 112 is opposite of backside 314 in FIG. 3 of radiation generation system 110 and detector system 112.

Figure 7:
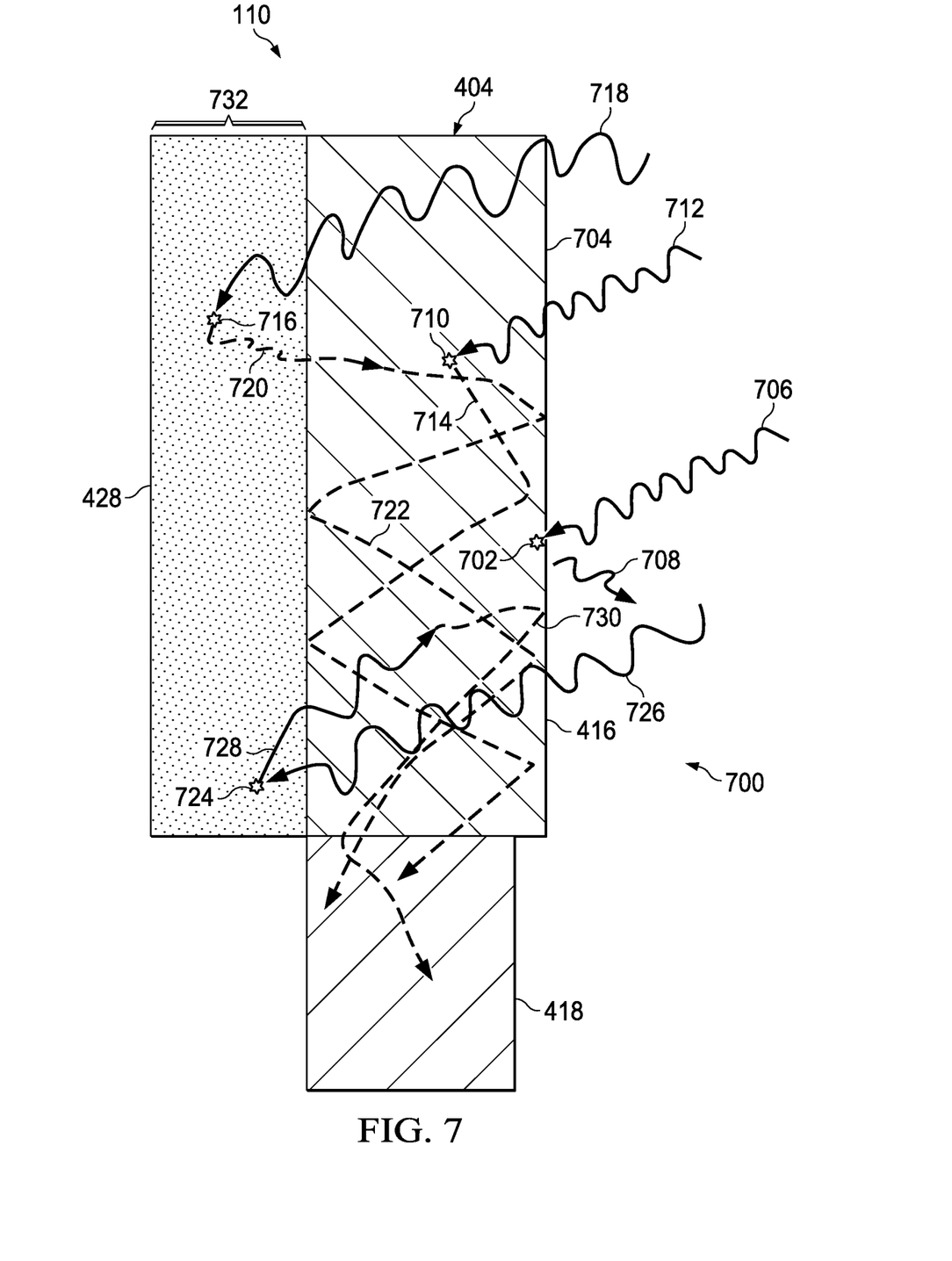
FIG. 7 is an polymer structure in accordance with an illustrative embodiment.

With reference next to FIG. 7, an illustration of a cross-sectional view of a sensor and a polymer structure is depicted in accordance with an illustrative embodiment. In this depicted example, a cross-sectional view of sensor 404 and polymer structure 428 taken along lines 7-7 in FIG. 6 is depicted.

In this illustrative example, polymer structure 428 is shown as associated with scintillator 416. Polymer structure 428 may be bonded to scintillator 416 using an adhesive. In other illustrative examples, polymer structure 428 may be associated with scintillator 416 using a mechanical connector such as a clamp, a frame, or other suitable structure.

In this view, x-ray photons 700 in backscatter 122 are shown. As depicted, x-ray photon 702 in x-ray photons 700 travels toward surface 704 of scintillator 416 as indicated by line 706. In this illustrative example, x-ray photon 702 may have an energy level of about 60 keV. This energy level may be insufficient to penetrate surface 704 of scintillator 416. Instead, x-ray photon 702 is reflected off of surface 704 as indicated by line 708.

X-ray photon 710 in x-ray photons 700 travels into scintillator 416 as indicated by line 712. In this illustrative example, x-ray photon 710 has an energy level of about 100 keV. In this illustrative example, the energy in x-ray photon 710 is absorbed by scintillator 416. As a result, a light signal is generated and travels into photomultiplier 418 as indicated by dotted line 714.

In this illustrative example, x-ray photon 716 in x-ray photons 700 travels through scintillator 416 into polymer structure 428 as indicated by line 718. In this illustrative example, x-ray photon 716 has an energy level of about 160 keV. Polymer structure 428 redirects x-ray photon 716 back into scintillator 416 as indicated by line 720. The energy in x-ray photon 716 is absorbed by scintillator 416. In response to absorbing the energy, another light signal is generated and travels into photomultiplier 418 as indicated by line 722.

In this illustrative example, x-ray photon 724 in x-ray photons 700 has an energy level of about 160 keV. As depicted, x-ray photon 724 also travels through scintillator 416 into polymer structure 428 as indicated by line 726. Polymer structure 428 redirects x-ray photon 724 back into scintillator 416 as indicated by line 728. Within scintillator 416, the energy in x-ray photon 724 is absorbed. In response, light is generated and travels into photomultiplier 418 as indicated by line 730.

As depicted, polymer structure 428 has thickness 732. In this example, thickness 732 of polymer structure 428 may have a value from about 0.5 inches to about 5.0 inches. Of course, thickness 732 may vary in other illustrative examples. Thickness 732 of polymer structure 428 may be selected such that a desired level of backscatter 122 is redirected to scintillator 416.

As the level of energy of x-ray photons 700 increases, the desired value for thickness 732 of polymer structure 428 also increases in these illustrative examples. For example, a larger value may be selected for thickness 732 of polymer structure 428 when x-ray photons 700 have an energy level of 100 keV than the value selected for thickness 732 of polymer structure 428 when x-ray photons 700 have an energy level of 60 keV. As a result, thickness 732 may be selected such that a desired level of backscatter 122 reaches scintillator 416 in these illustrative examples. Alternatively, the material for polymer structure 428 may be changed to reduce increases in thickness 732.

As can be seen, polymer structure 428 causes more x-ray photons 700 to be absorbed by scintillator 416 and turned into light than would occur in the absence of polymer structure 428. The intensity of this light generated from x-ray photons 700 being absorbed by scintillator 416 may be proportional to the characteristics of x-ray photons 700. These characteristics may be, for example, without limitation, collision characteristics and the amount of energy of x-ray photons 700. In some illustrative examples, only some of x-ray photons 700 are absorbed by scintillator 416, even when polymer structure 428 is present.

Figure 8:
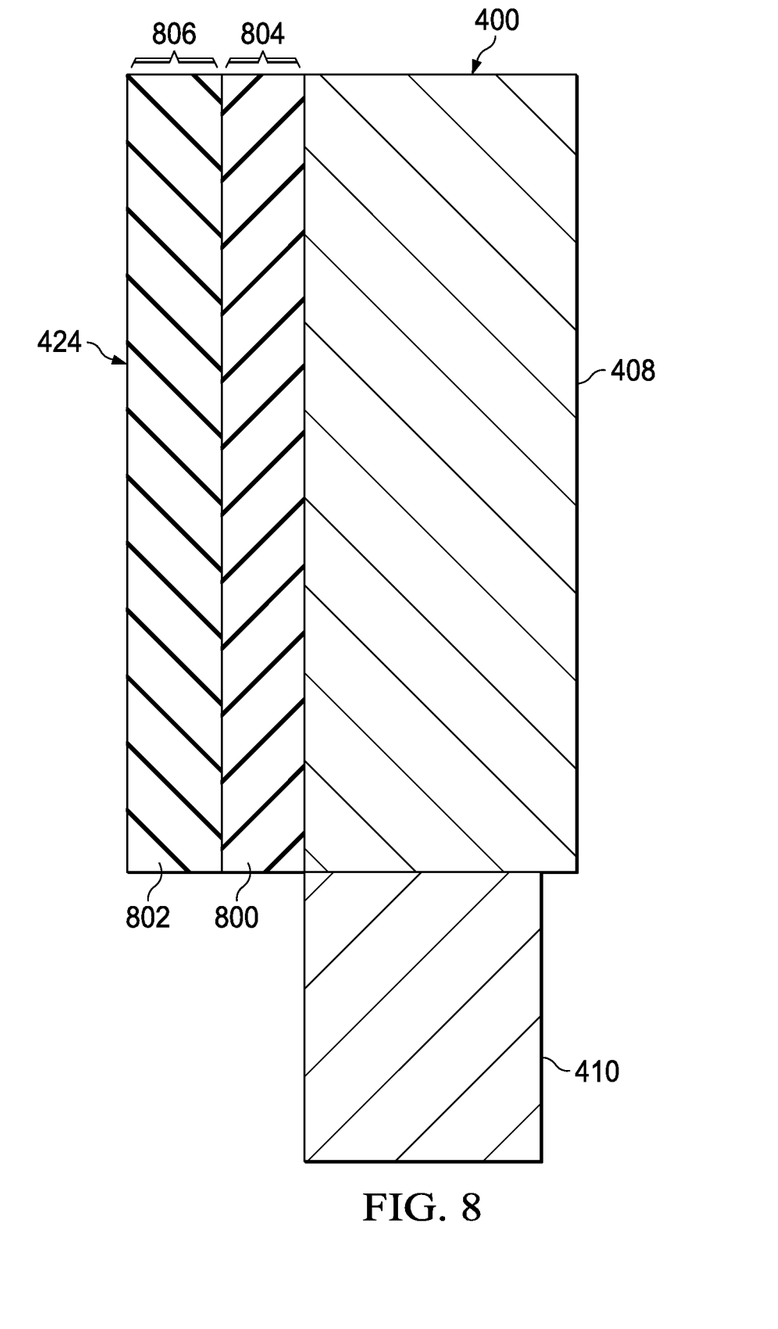
FIG. 8 is an illustration of a cross-sectional view of a sensor and a polymer structure in accordance with an illustrative embodiment.

Turning now to FIG. 8, an illustration of a cross-sectional view of a sensor and a polymer structure is depicted in accordance with an illustrative embodiment. In this depicted example, a cross-sectional view of sensor 400 in polymer structure 424 is shown taken along lines 8-8 in FIG. 6. Polymer structure 424 is shown as being associated with scintillator 408.

As can be seen in this illustrative example, polymer structure 424 is comprised of layer 800 and layer 802. In these illustrative examples, layer 800 has thickness 804 and layer 802 has thickness 806. Thickness 804 may be the same as thickness 806 or the thicknesses may have different values.

For example, the materials for layer 800 and layer 802 may be selected to have different densities, types of materials, or both. The densities may be selected to redirect x-ray photons 700 in FIG. 7 at different levels of power. Thickness 804 for layer 800 and thickness 806 for layer 802 also may be selected to redirect x-ray photons 700 and different levels of power. In other words, the materials and thicknesses may be selected to redirect a particular range of energy levels of x-ray photons 700.

As depicted, layer 800 and layer 802 are associated with each other. Layer 800 and layer 802 may be comprised of a number of different types of materials. Layer 800 and layer 802 may be comprised of the same material or different materials.

Figure 9:
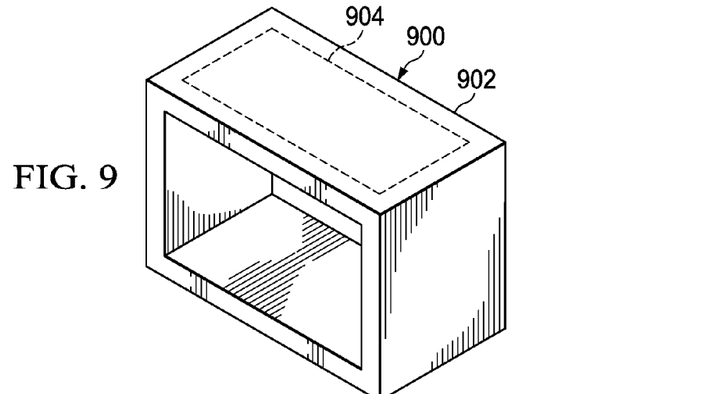
FIG. 9 is an illustration of a sensor with a polymer structure in accordance with an illustrative embodiment.

Turning now to FIG. 9, an illustration of a sensor with a polymer structure is depicted in accordance with an illustrative embodiment. In this illustrative example, sensor 900 is shown as being associated with polymer structure 902.

In this illustrative example, polymer structure 902 is shown in the shape of an open cube. In this view, scintillator 904 in sensor 900 is shown as being located within polymer structure 902.

The illustration of backscatter inspection system 106 and the different components in backscatter inspection system 106 in FIG. 1 and FIGS. 3-9 is not meant to imply limitations to the manner in which other backscatter inspection systems may be implemented. For example, although four sensors are shown in detector system 112, other numbers of sensors may be used. For example, two sensors, eight sensors, or some other number of sensors may be included. As another example, the polymer structures may have other shapes other than rectangular shapes. For example, the polymer structures may have a shape that is square, pentagonal, octagonal, or some other suitable shape.

Further, although polymer structures are shown in these examples, other types of carbon-based structures may be used. Other types of carbon-based structures may include, for example, without limitation, ultra-high-molecular-weight polyethylene, acrylic, polycarbonate, polypropylene, high-density polyethylene, low-density polyethylene, vinyl, acrylonitrile butadiene styrene, polyvinyl chloride, and other suitable carbon-based materials.

Although polymer structure 424 is shown as having a single layer and double layer in FIG. 7 and FIG. 9, other illustrative examples may include other numbers of layers. For example, polymer structure 424 may have four layers, eight layers, or some other suitable number of layers.

The different components shown in FIG. 1 and FIGS. 3-9 may be combined with components in FIG. 2, used with components in FIG. 2, or a combination of the two. Additionally, some of the components in FIG. 1 and FIGS. 3-9 may be illustrative examples of how components shown in block form in FIG. 2 can be implemented as physical structures.

Figure 10:
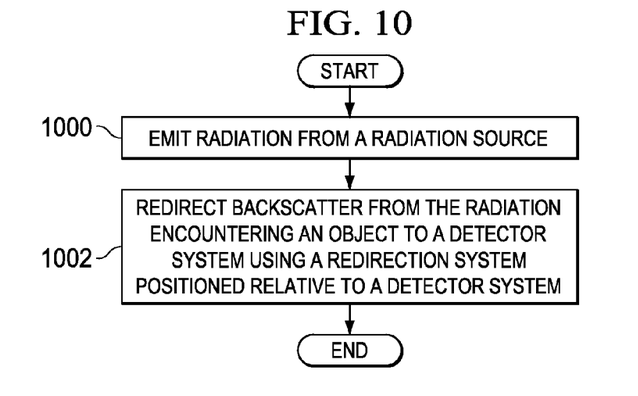
FIG. 10 is an illustration of a flowchart of a process for inspecting an object in accordance with an illustrative embodiment.

Turning now to FIG. 10, an illustration of a flowchart of a process for inspecting an object is depicted in accordance with an illustrative embodiment. The process illustrated in FIG. 10 may be implemented in inspection environment 200 to inspect object 206 in FIG. 2. In particular, one or more of the different operations may be implemented using backscatter inspection system 204 in FIG. 2.

The process begins by emitting radiation from a radiation source (operation 1000). Thereafter, backscatter is redirected from the radiation encountering an object to a detector system using a redirection system positioned relative to a detector system (operation 1002) with the process terminating thereafter.

Figure 11:
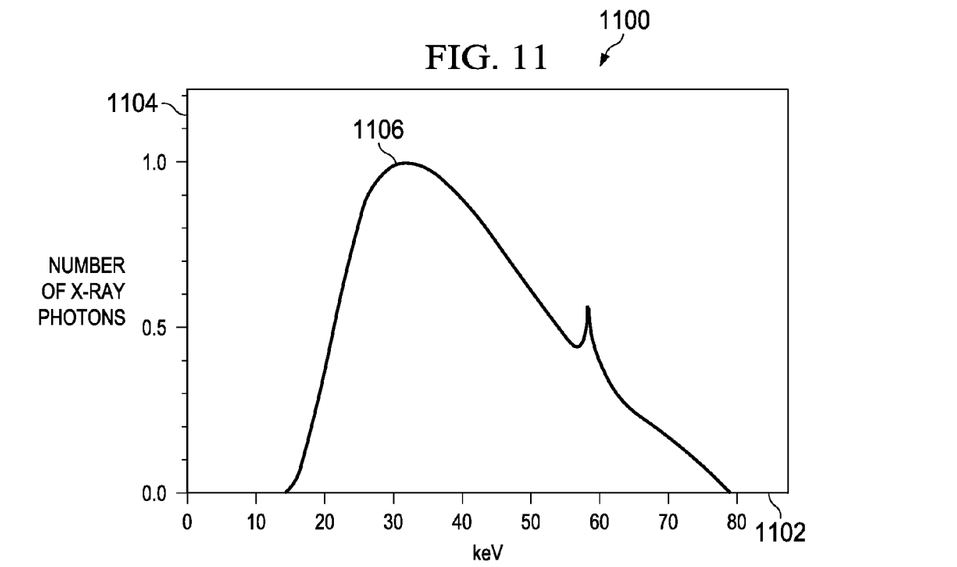
FIG. 11 is an illustration of a graph of a spectrum of energy levels in backscatter in accordance with an illustrative embodiment.

Turning now to FIG. 11, an illustration of a graph of a spectrum of energy levels in backscatter is depicted in accordance with an illustrative embodiment. In this illustrative example, graph 1100 illustrates backscatter that may occur from a beam of x-rays directed toward an object. In this example, the object may be comprised of tungsten.

As depicted, x-axis 1102 represents a level of energy in keV. Y-axis 1104 represents a number of x-ray photons. In this illustrative example, the level of energy for x-ray photons in the backscatter range from about 15 keV to about 80 keV.

Line 1106 indicates the number of x-ray photons at different levels of energy in the backscatter. As can be seen in this illustrative example, line 1106 is illustrative of a Bremsstrahlung x-ray distribution. Further, a greater number of x-ray photons may be located from about 20 keV to about 40 keV.

When backscatter inspection system 204 in FIG. 2 is used, backscatter inspection system 204 is configured to detect x-ray photons in a broader range of energy levels. In these illustrative examples, backscatter inspection system 204 with redirection system 221 may detect x-ray photons in backscatter 236 in a manner that provides for an increased contrast in pixels in image data 210 in FIG. 2.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams. In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 12:
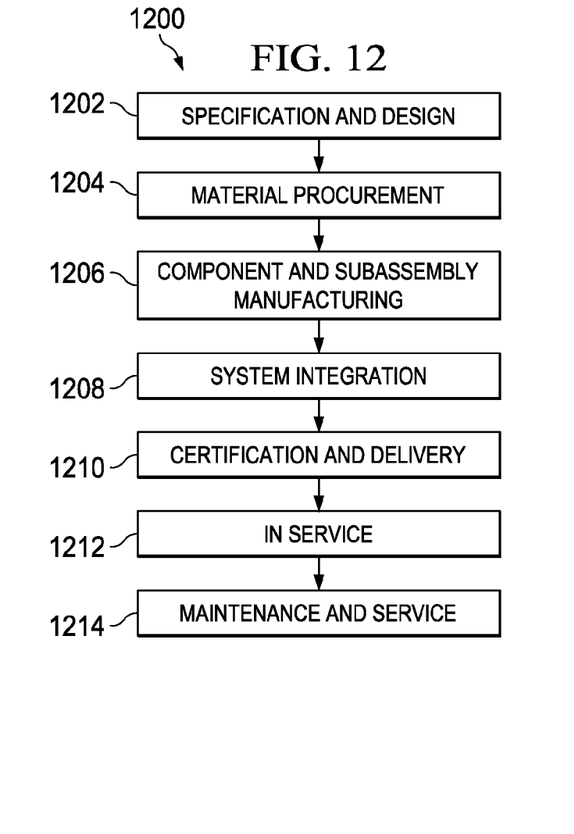
FIG. 12 is an illustration of an aircraft manufacturing and service method in accordance with an illustrative embodiment.
Figure 13:
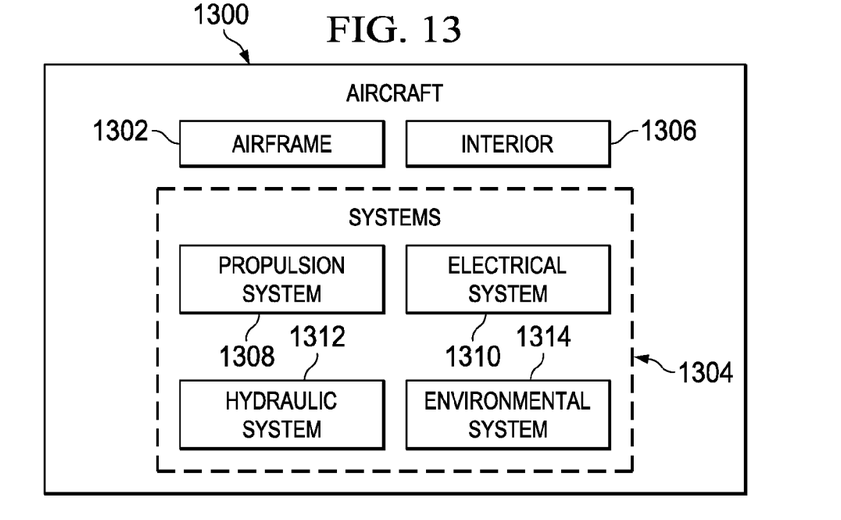
FIG. 13 is an illustration of an aircraft in which an illustrative embodiment may be implemented.

Illustrative embodiments of the disclosure may be described in the context of aircraft manufacturing and service method 1200 as shown in FIG. 12 and aircraft 1300 as shown in FIG. 13. Turning first to FIG. 12, an illustration of an aircraft manufacturing and service method is depicted in accordance with an illustrative embodiment. During pre-production, aircraft manufacturing and service method 1200 may include specification and design 1202 of aircraft 1300 in FIG. 13 and material procurement 1204.

During production, component and subassembly manufacturing 1206 and system integration 1208 of aircraft 1300 in FIG. 13 takes place. Thereafter, aircraft 1300 in FIG. 13 may go through certification and delivery 1210 in order to be placed in service 1212. While in service 1212 by a customer, aircraft 1300 in FIG. 13 is scheduled for routine maintenance and service 1214, which may include modification, reconfiguration, refurbishment, and other maintenance or service.

Each of the processes of aircraft manufacturing and service method 1200 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 13, an illustration of an aircraft is depicted in which an illustrative embodiment may be implemented. In this example, aircraft 1300 is produced by aircraft manufacturing and service method 1200 in FIG. 12 and may include airframe 1302 with plurality of systems 1304 and interior 1306. Examples of systems 1304 include one or more of propulsion system 1308, electrical system 1310, hydraulic system 1312, and environmental system 1314. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1200 in FIG. 12. One or more of the illustrative embodiments may be implemented during component and subassembly manufacturing 1206. For example, a backscattering system in accordance with an illustrative embodiment may be used to inspect objects, such as parts manufactured during component and subassembly manufacturing 1206.

Additionally, an illustrative embodiment may be implemented during system integration 1208. An illustrative embodiment may be implemented during this stage to inspect parts after their assembly and integration. Further, an illustrative embodiment also may be implemented during maintenance and service 1214 to perform inspections of objects during routine maintenance, upgrades, rework, and other operations that may occur during maintenance and service 1214. The use of a number of the different illustrative embodiments may substantially expedite the assembly of and/or reduce the cost of aircraft 1300.

Thus, with one or more illustrative embodiments, an amplified x-ray backscatter inspection system may be implemented to inspect objects. A backscatter inspection system implemented in accordance with an illustrative embodiment may provide an ability to generate image data with less loss in contrast in resolution. By redirecting x-ray photons, a loss in contrast in resolution may be reduced from x-ray photons that may pass through a sensor or may not penetrate the sensor sufficiently to generate light in the scintillator in the sensor.

With redirection systems in accordance with an illustrative embodiment, a broader range of energy levels for x-ray photons can be detected in these illustrative examples. For example, in a backscatter inspection system implemented in accordance with an illustrative embodiment, the amount of backscatter that may be detected may be increased by as much as about 30 percent as compared to currently used backscatter inspection systems. In other words, the signal-to-noise ratio in generating image data from backscatter may be increased by as much as about 30 percent in these illustrative examples.

As a result, larger power supplies and x-ray tubes to obtain levels of energy for x-ray photons that may be detected by currently used detectors may be avoided. Thus, the size, weight, and expense of backscatter inspection systems may be reduced.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising: a radiation generation system configured to emit x rays; a detector system configured to detect backscatter formed in response to the x-rays encountering an object, the detector system comprising sensors; and
    a redirection system positioned relative to the detector system and configured to redirect the backscatter to the detector system, the redirection system comprising redirection structures, and wherein the sensors of the detector system are positioned between the redirection structures of the redirection system and the object.

2. The apparatus of claim 1, wherein the redirection structures are configured to reflect the backscatter to the detector system.

3. The apparatus of claim 1, wherein the redirection system is associated with the detector system.

4. The apparatus of claim 2, wherein the redirection structures are selected from at least one of a panel, a flat panel, a curved panel, a portion of a hollow sphere, a portion of a hollow cube, a housing, a frame, or other suitable forms.

5. The apparatus of claim 1, wherein the redirection system is comprised of a number of materials selected from at least one of a polymer, a polyurethane, a plastic, or a hydrocarbon-based material.

6. The apparatus of claim 1, wherein the redirection system is configured to redirect the backscatter having an energy level from about 120 keV to about 450 keV to the detector system.

7. The apparatus of claim 1, wherein the sensors are configured to detect the backscatter.

8. The apparatus of claim 7, wherein a sensor in the number of sensors comprises at least one of a scintillator or a light detector.

9. The apparatus of claim 1, wherein the radiation generation system comprises:
    a radiation source configured to emit the x-rays; and
    a collimator configured to form a beam of the x rays using a portion of the x-rays emitted by the radiation source.

10. The apparatus of claim 9, wherein the radiation comprises x-rays.

11. The apparatus of claim 1, wherein the radiation generation system, the detector system, and the redirection system form a backscatter inspection system further comprising:
    a moveable platform, wherein the inspection system is associated with the moveable platform.

12. A method for inspecting an object, the method comprising:
    emitting x-rays from a radiation source; and
    redirecting backscatter from the x-rays encountering the object to a detector system using a redirection system positioned relative to the detector system, wherein sensors of the detector system are positioned between redirection structures of the redirection system and the object.

13. The method of claim 12 further comprising:
    emitting the x-rays as a beam of the x rays from the radiation source.

14. The method of claim 12 further comprising:
    generating image data from the backscatter detected by the detector system.

15. The method of claim 12, wherein the radiation comprises x-rays.

16. The method of claim 12, wherein the redirection structures of the redirection system are configured to reflect the backscatter to the detector system.

17. The method of claim 16, wherein the redirection structures are selected from at least one of a panel, a flat panel, a curved panel, a portion of a hollow sphere, a portion of a hollow cube, a housing, a frame, or other suitable forms.

18. The method of claim 12, wherein the redirection system is comprised of a number of materials selected from one of a polymer, a polyurethane, a plastic, or a hydrocarbon-based material.

19. The apparatus of claim 1, wherein the radiation generation system comprises a collimation wheel with a collimator and a radiation source within the collimation wheel, wherein the sensors of the detector system are configured to detect the backscatter, and wherein the radiation generation system is positioned such that the x-rays emitted travel between two of the sensors and towards the object.

20. The method of claim 13, wherein the radiation source comprises a collimation wheel with a collimator and an x-ray source within the collimation wheel, wherein the sensors of the detector system are configured to detect the backscatter, and wherein the radiation source is positioned such that the x-rays emitted travel between two of the sensors and towards the object.

\* \* \* \* \*